US010792515B2

(12) United States Patent
    Schadewaldt et al.

(10) Patent No.: US 10,792,515 B2
(45) Date of Patent: Oct. 6, 2020

(54) METHOD FOR DETERMINING A PATIENT SPECIFIC LOCALLY VARYING MARGIN

(71) Applicant: KONINKLIJKE PHILIPS N.V., Eindhoven (NL)

(72) Inventors: Nicole Schadewaldt, Norderstedt (DE); Jochen Peters, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 11 days.

(21) Appl. No.: 15/775,021

(22) PCT Filed: Dec. 16, 2016

(86) PCT No.: PCT/EP2016/081620
 § 371 (c)(1),
 (2) Date: May 10, 2018

(87) PCT Pub. No.: WO2017/103237
 PCT Pub. Date: Jun. 22, 2017

(65) Prior Publication Data
 US 2018/0318604 A1  Nov. 8, 2018

(30) Foreign Application Priority Data
 Dec. 18, 2015 (EP) .................................... 15201291

(51) Int. Cl.
  *G06K 9/00* (2006.01)
  *A61N 5/10* (2006.01)
(52) U.S. Cl.
  CPC ......... *A61N 5/1037* (2013.01); *A61N 5/1039* (2013.01); *A61N 5/1038* (2013.01)
(58) Field of Classification Search
  CPC .. A61N 5/1036; A61N 5/1037; A61N 5/1038; A61N 5/1039; A61N 5/1048;
  (Continued)

(56) References Cited

U.S. PATENT DOCUMENTS 9,076,222 B2  7/2015 Bal
2008/0144772 A1  6/2008 Yi et al.
(Continued)

OTHER PUBLICATIONS

Steiner, E. et al. "Prostate and Patient Intrafraction Motion: Impact on Treatment Time-Dependent Planning Margins for Patients with Endorectal Balloon", IJROBP vol. 86, No. 4, pp. 755e761, 2013.
(Continued)

*Primary Examiner* — Gabriel I Garcia

(57) ABSTRACT

It is an object of the invention to provide for an improved radiation treatment. According to a first aspect of the invention, this object is achieved by a method for determining a patient specific locally varying margin on a treatment target and/or an organ at risk in order to compensate for local intrafraction motion expected during a radiotherapy fraction to be delivered over a radiotherapy fraction time interval. The patient specific locally varying margin is determined based on a displacement and/or an estimate of the displacement of at least a first location and a second location on the treatment target and/or organ at risk. The method comprises steps of: acquiring a first medical image of the treatment target and/or the organ at risk and acquiring a second medical image of the treatment target and/or the organ at risk, wherein the time between the acquisition of the first medical image and the second medical image is similar to the radiotherapy fraction time interval and determining of positions of the first location and the second location in the first medical image and in the second medical image and using the determined positions for determining the patient specific locally varying margin around the treatment target and/or organ at risk.

21 Claims, 5 Drawing Sheets

(58) Field of Classification Search
CPC ......... A61B 5/00; A61B 5/0033; A61B 5/004;
A61B 5/107; A61B 6/00; A61B 6/50;
A61B 6/52; A61B 6/5241; A61B 6/5247
USPC ....... 382/128, 131, 173, 174, 256, 282, 283,
382/308, 325; 600/1, 411
See application file for complete search history.

(56) References Cited

U.S. PATENT DOCUMENTS

| | | |
|---|---|---|
| 2012/0022363 A1 | 1/2012 | Dempsey |
| 2012/0264996 A1 | 10/2012 | Chen et al. |
| 2014/0073833 A1 | 3/2014 | Khan et al. |
| 2017/0100078 A1* | 4/2017 | Han .................. G16H 50/50 |
| 2017/0103287 A1* | 4/2017 | Han .................... G06T 5/00 |
| 2018/0174298 A1* | 6/2018 | Schadewaldt .......... A61B 5/055 |

OTHER PUBLICATIONS

Van Herk, M. et al., "The probability of correct target dosage: dose-population histograms for deriving treatment margins in radiotherapy", International Journal of Radiation Oncology, Biology, Physics, Jul. 1, 2000, pp. 1121-1135.

Löf, J. et al., "An adaptive control algorithm for optimization of intensity modulated radiotherapy considering uncertainties in beam profiles, patient set-up and internal organ motion", Physics in Medicine and Biology, Institute of Physics Publishing, Bristol GB, vol. 43, Jun. 1, 1998, pp. vol. 43, Abstract.

\* cited by examiner

METHOD FOR DETERMINING A PATIENT SPECIFIC LOCALLY VARYING MARGIN

FIELD OF THE INVENTION

The invention relates to the field of radiation therapy.

BACKGROUND OF THE INVENTION

Radiation therapy planning is a complex process, comprising four steps:
1. On a given patient image a treatment target and one or more organs at risk are delineated (manually or by (semi-) automatic methods).
2. Several margins for irradiation inaccuracy, patient motion, or sub-clinical cancer cells outside the visible tumor are added.
3. Then the treatment target and one or more organs at risk are equipped with a number of objectives for the radiation, e.g. maximal/minimal doses.
4. Then a computer program optimizes beam parameters to get as close as possible to those objectives.

The challenge in the whole process is to distribute a high dose to the cancer cells and a low dose to the healthy cells, especially to sensitive organs at risk. For this, a number of unknown parameters have to be estimated, e.g., the tumor spread, the patient motion and positioning inaccuracy. This estimation must achieve a fine balance between sufficient dose to the treatment target while keeping organs at risk below a maximum tolerable dose.

Often, the patient motion is compensated for with a margin or treatment margin all around a specific structure (treatment target or organ at risk). There are efforts to quantify systematic errors and include them in radiotherapy planning, e.g., by elongating a target volume in the lung with the help of a breathing phase reconstructed 4D CT. Furthermore, some motion uncertainty is being compensated by strict behavioral protocols, such as drinking and eating protocols for prostate patients to achieve a consistent bladder and rectum filling during irradiation.

Steiner, E. et al. Prostate and Patient Intrafraction Motion: Impact on Treatment Time-Dependent Planning Margins for Patients With Endorectal Balloon, IJROBP Vol. 86, No. 4, pp. 755e761, 2013 describes the determination of motion for a patient group during treatment.

SUMMARY OF THE INVENTION

It is an object of the invention to provide for an improved radiation treatment. According to a first aspect of the invention, this object is achieved by a method according to claim 1.

Some patient motion during radiotherapy is highly inhomogeneous and varies greatly between individuals. Examples are the filling of the bladder or movement of the rectum during the time of prostate irradiation. Currently, this motion is compensated for with generic margins around the treatment target and/or organ at risk.

It is an insight of the inventors that although some motion is highly variable between individuals, it is quite specific and reproducible for a given individual. Also, motion quantification can be location specific: there could be regions of the treatment target and/or organ at risk, which will not move due to outer forces: e.g., because of bone restrictions.

It is a further insight of the inventors that the use of patient specific and a locally varying margin may therefore better suit the situation for the individual patient. By using such a margin one may achieve a better balance between sufficient dose to the treatment target while keeping organs at risk below a maximum tolerable dose. By having two medical images with a time interval between the acquisition of the first medical image and the second medical image, which is similar to the radiotherapy fraction time interval, a patient specific and locally varying margin can be determined, which is representative for the patient and location specific displacement of the treatment target and/or organ at risk during the radiotherapy fraction. Thereby, radiation treatment may be improved. This application focused on margins to compensate for intrafraction motion. Those skilled in the art may want to extent those margins further for example to in addition compensate for sub-clinical cancer cells or set up errors.

The first and second location could be anatomical landmarks, but they could also be implanted markers.

According to embodiments of the invention, more than 2 medical images are acquired over the acquisition time interval. The patient specific and locally varying margin is determined based on a measure of variation in the positions of the first and second locations. This measure could for example be the maximum variation or some percentage (e.g. 95%) of the maximum variation.

In addition to compensating for intrafraction the patient specific and a locally varying margin could also be used for compensating for interfraction motion. i.e. over several days. This could be achieved by acquiring images, preferably MRI images, at multiple days before the real treatment starts. Another option is to use an MRI guided radiotherapy system and to start the treatment with a more general margin to compensate for interfraction motion. Every treatment fraction MRI images can be acquired from the patient. These images can then be used to calculate the patient specific and a locally varying margin to be used to compensate for interfraction motion/changes.

The method according to claim 1 comprises the step of acquiring a first medical image and a second medical image. Preferably, the first and second medical image are CT images and more preferably the first and second medical images are MRI images.

According to embodiments of the invention, the patient specific margin is determined based on multiple locations defining a first contour around the treatment target or organ at risk in the first medical image and defining a second contour around the treatment target or organ at risk in the second medical image. This is advantageous, because the more locations are used to determine the locally varying margin, the more the margin can be adapted to the local situation and movement. Preferably, the margin is continuously varying around the treatment target and/or organ at risk. This embodiment is also advantageous because it allows the determination of the patient specific locally varying margin by means of segmentation of the treatment target and/or organ at risk.

According to further embodiments of the invention, the method further comprises the step of calculating a radiotherapy plan using the patient specific locally varying margin. This is advantageous, because it may lead to an improved radiotherapy plan.

According to further embodiments of the invention, multiple margins are determined, such that during the radiotherapy fraction a time dependent margin can be used. The multiple margins are taken into account for the calculation of the radiotherapy plan. This is advantageous, because during the radiation treatment the treatment target and/or organ at risk may (slowly) move to a different position and/or may (slowly) change shape, such that the margin used at the start of the treatment fraction is not optimal to suit the situation at a later stage during the treatment fraction. Examples of such motion or shape changes could be bladder filling, bowel motion or overall relaxation of the patient during the treatment fraction.

According to further embodiments of the invention, the first medical image is an MRI image suitable to be used for a generation of a pseudo CT image of the treatment target. This could for example be a T1-DIXON or UTE-DIXON image. This embodiment is advantageous, because in this way an image that needs to be acquired anyway in an MRI based radiotherapy workflow can in addition be used to determine the patient specific locally varying margin.

According to further embodiments of the invention, the second medical image is an image suitable to be used for segmentation of the treatment target. This could for example be a T2w image. This embodiment is advantageous, because in this way an image that needs to be acquired anyway in order to delineate the treatment target can be used in addition to determine the patient specific locally varying margin. This embodiment is even more advantageous when the second medical image is an MRI image and when the first medical image is an MRI image suitable to be used for a generation of a pseudo CT image of the treatment target. This is even more advantageous, because in this way the images that need to be acquired anyway to support an MRI based radiotherapy planning can be used in addition to determine the patient specific locally varying margin. In this way, the information on which the patient specific locally varying margin is based can be almost or completely obtained for free in the sense that no extra time is needed for the image acquisition.

According to further embodiments of the invention, the method further comprises a step of displaying the displacement of the first location and the displacement of the second location between the acquisition of the first medical image and the acquisition of the second medical image to a user. This is advantageous, because it may be more insightful for a clinician responsible for the radiation treatment.

According to further embodiments of the invention, the method further comprises a step of calculating an interpolated position and/or extrapolated position of the first location and the second location and displaying the interpolated position and/or extrapolated position to the user. This embodiment is advantageous, because it provides the clinician more freedom on how to apply a margin. The positions determined by the first medical image could be assumed to be at 0%. The positions determined by the second medical image could be assumed to be at 100%. If a clinician wants to be on the safe side for a certain structure, he may want to apply a margin on the extrapolated positions or contour (e.g. 120%). In this way he is more certain that the objectives for this structure will be met in practice. On the other hand, conservative margins on one structure may make it more complicated to meet the objectives for the other structures. Therefore, the clinician may also want to choose an interpolated margin for some structures.

According to further embodiments of the invention the position of the first and second location are determined based on segmentation of the treatment target and/or organ at risk. This is advantageous because this method is relatively easy to automate and will thereby result in more reproducible results. Segmentation is not the only way how positions could be determined. Alternative solutions are known to the skilled person, e.g. he could decide to look for the displacement of individual landmarks in the first medical image and second medical image.

According to a further aspect of the invention, this object is also achieved according to computer program product according to claim 12. This computer program product is configured for image analysis. This is advantageous, because in this way image analysis could also be performed at a stand-alone workstation. According to further embodiments the computer program product further comprises program code means for causing a computer to carry out the steps of a method of acquiring the first medical image of the treatment target and/or organ at risk and acquiring the second medical image of the treatment target and/or organ at risk, wherein the time between the acquisition of the first medical image and the second medical image is similar to a radiotherapy fraction time interval. This embodiment is especially advantageous when the computer program product is installed on a medical imaging system. In this way, the medical image system can analyze the image directly after acquisition. According to further embodiments of the invention, the computer program product is configured to perform any of the method steps described above.

According to a further aspect of the invention, this object is achieved by a medical imaging system according to claim 15. The medical imaging system could be configured such that it is suitable to perform any of the methods described above.

These and other aspects of the invention will be apparent from and elucidated with reference to the embodiments described hereinafter.

DETAILED DESCRIPTION OF THE INVENTION

Figure 1:
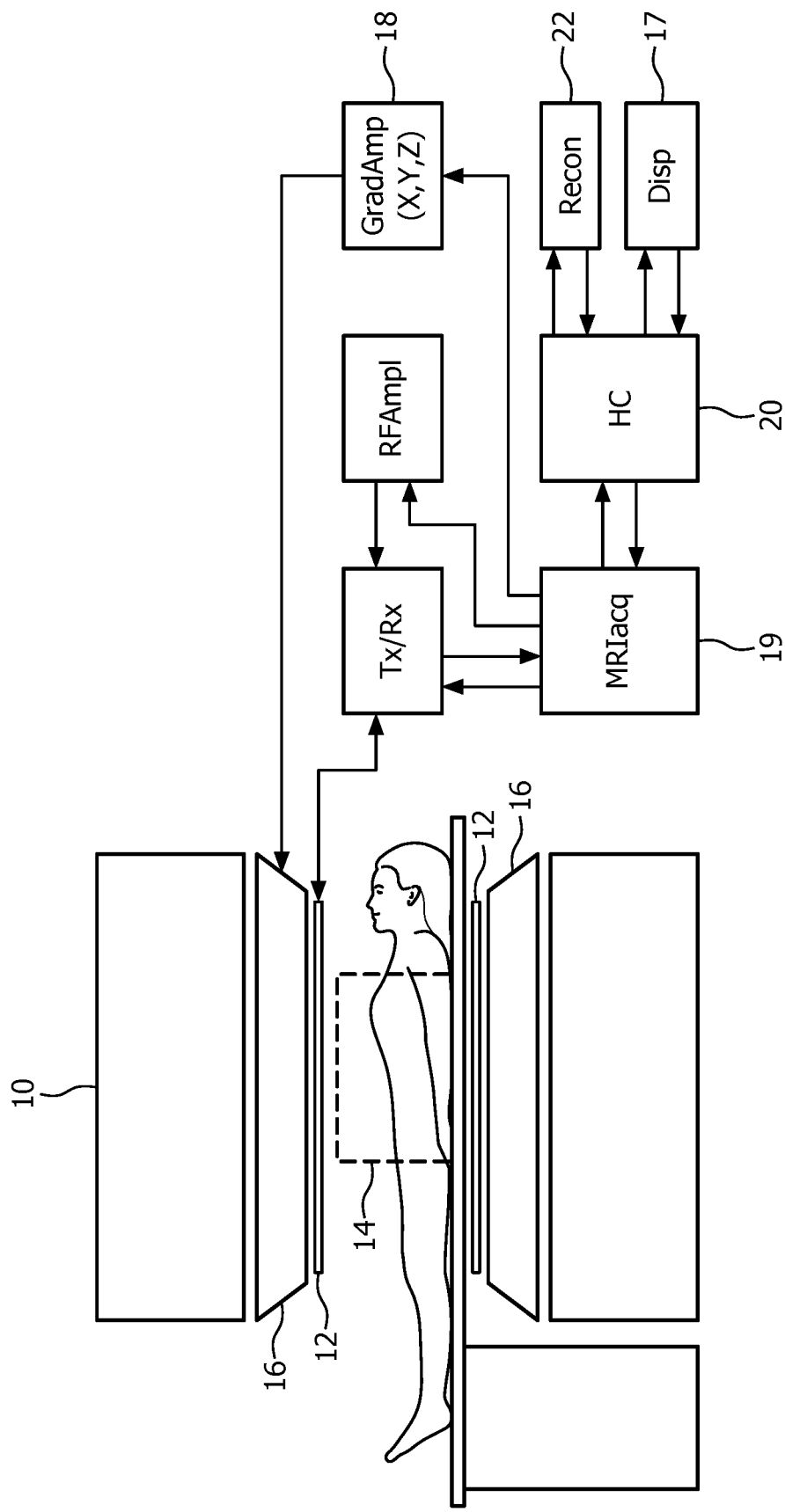
FIG. 1 illustrates diagrammatically a medical imaging system.

FIG. 1 illustrates diagrammatically a medical imaging system, in this case a magnetic resonance imaging (MRI) system in which the invention is used. The MRI system comprises a main magnet 10 which generates a steady homogeneous main magnetic field within the examination zone 14. This main magnetic field causes a partial orientation of the spins in the object to be examined along the field lines of the main magnetic field. An RF system is provided with one or more RF antennae 12 to emit an RF excitation electromagnetic field into the examination zone 14 to excite spins in the body of the object to be examined. The relaxing spins emit magnetic resonance signals in the RF range which are picked up by the RF antennae 12, notably in the form of RF receiving coils. Further, gradient coils 16 are provided to generate temporary magnetic gradient fields, notably read gradient pulses and phase encoding gradients. These gradient fields usually are orientated in mutual orthogonal directions and impose spatial encoding on the magnetic resonance signals. Gradient amplifiers (GradAmp(x,y,z)) 18 are provided to activate the gradient coils 16 to generate the magnetic gradient encoding fields. The magnetic resonance signals picked up by the RF receiver antennae 12 are applied to an MRI data acquisition (MRIacq) 19 system which comprises a spectrometer. The MRI data acquisition system provides the data to a host computer (HC) 20, which in turn provides it to a reconstructor (Recon) 22, which reconstructs an image from the data. The host computer could further comprise a computer program product, which will be configured to perform the methods steps as described below.

Figure 2:
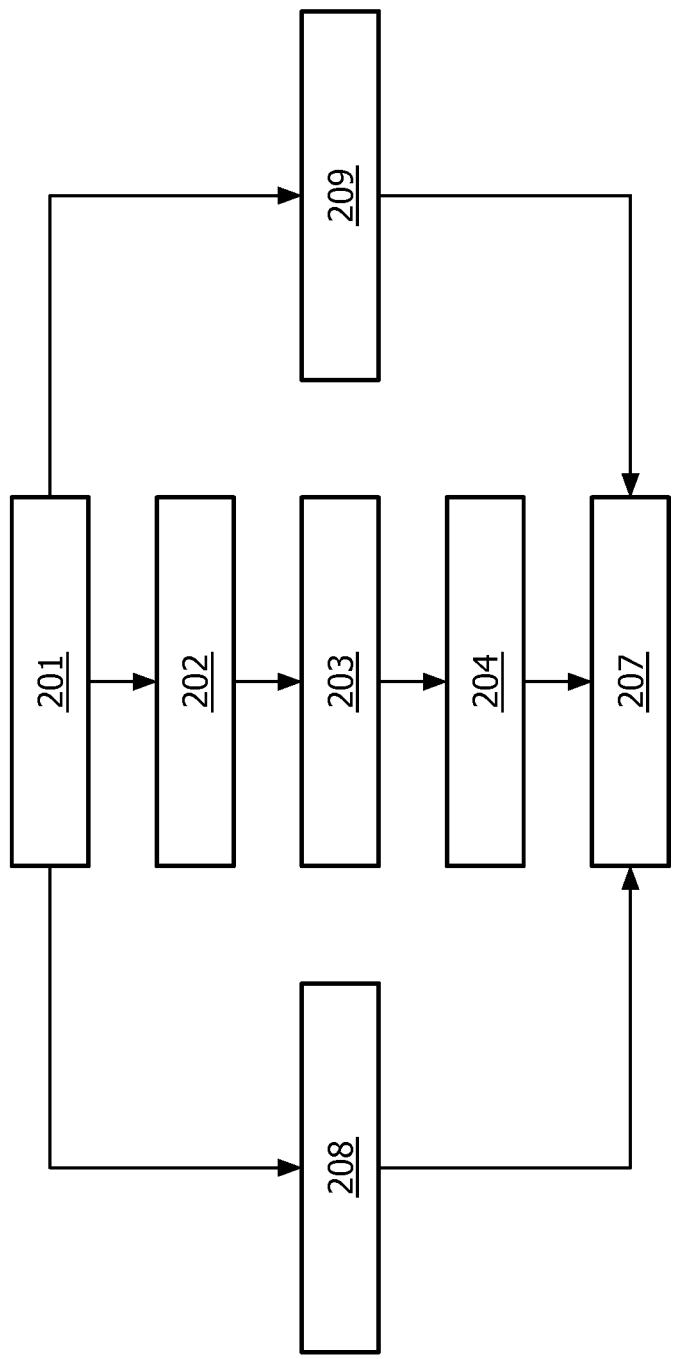
FIG. 2 illustrates diagrammatically a method according to the invention.
Figure 3:
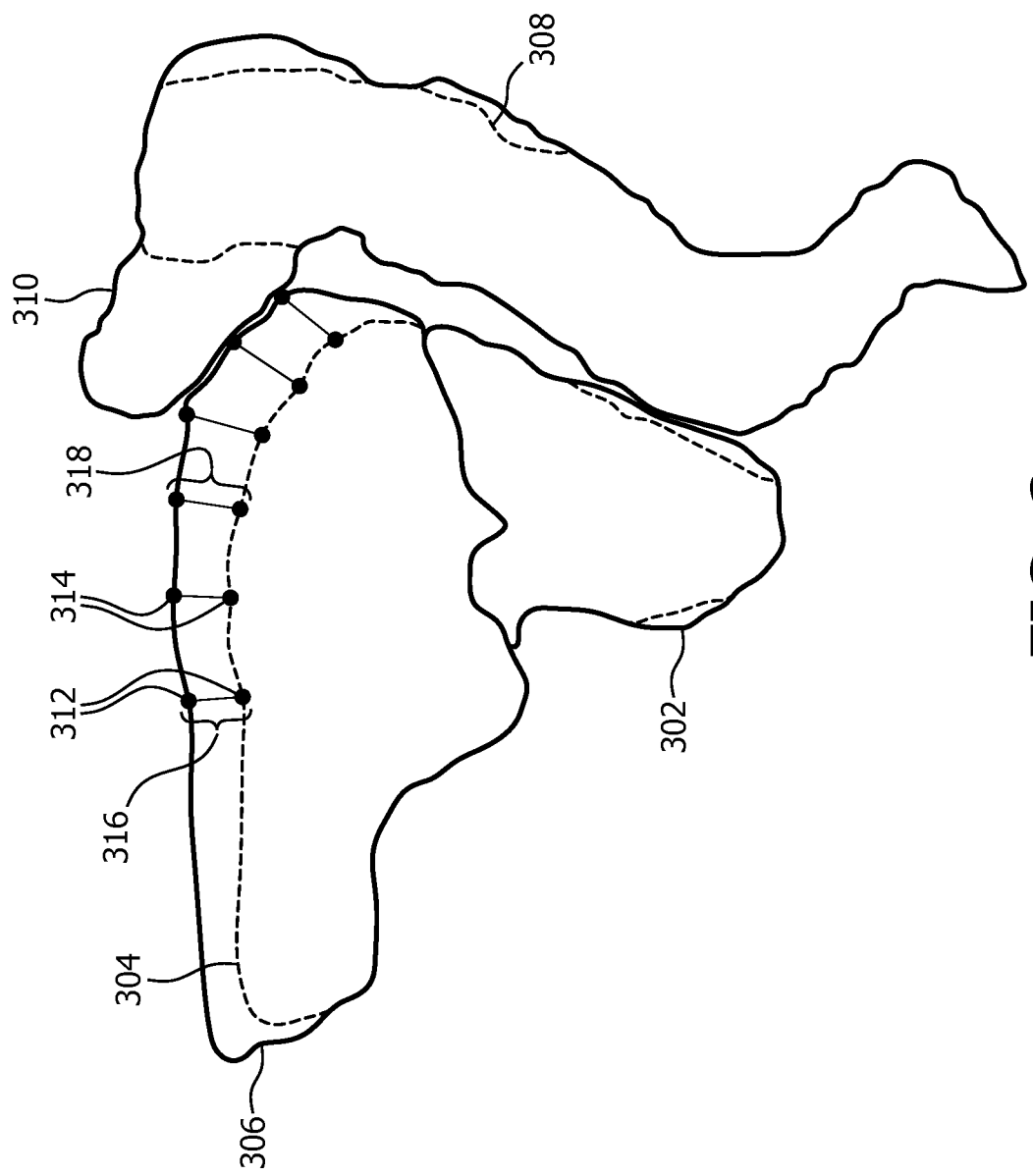
FIG. 3 illustrates diagrammatically segmentations of a treatment target and organs at risk based on a first medical image and a second medical image and FIG. 4 shows a few examples of how the displacement of the first location, second location and optionally further locations can be displayed to a user

FIG. 2 illustrates diagrammatically a method according to the invention. FIG. 2 is a flow chart. The method is further illustrated by means of the example shown in FIG. 3. FIG. 3 illustrates diagrammatically segmentations of a treatment target and organs at risk based on a first medical image and a second medical image.

The method according to embodiments of the invention is a method for determining a patient specific locally varying margin on a treatment target 302 (FIG. 3) and/or an organ at risk 304, 308 (FIG. 3) in order to compensate for local intrafraction motion expected during a radiotherapy fraction to be delivered over a radiotherapy fraction time interval. The radiotherapy time interval is dependent on the organ to be treated and on the complexity of the radiotherapy plan. The organ to be treated is known beforehand and the clinician can decide beforehand about the desired complexity of the plan (e.g. conformal, intensity modulated radiotherapy, VMAT). Therefore, the radiotherapy time interval is predictable before the actual creation of the radiotherapy plan. For a prostate cancer treatment the radiotherapy time interval is nowadays most often between 5-15 minutes. The patient specific locally varying margin is determined based on a displacement and/or an estimate of the displacement of at least a first location 312 (FIG. 3) and a second location 314 (FIG. 3) on the treatment target and/or organ at risk. The method to determine the patient specific locally varying margin comprises the following steps:

Acquiring a first medical image of the treatment target and/or the organ at risk 201. The first medical image could for example be a UTE-DIXON MRI or a T1-DIXON image. This UTE-DIXON image could in step 208 be used to generate a pseudo-CT or attenuation map. In turn, the pseudo-CT or attenuation map could serve as an input for the calculation of a radiotherapy plan 208.

Acquiring a second medical image of the treatment target and/or the organ at risk 202, wherein the time between the acquisition of the first medical image and the second medical image is similar to the radiotherapy fraction time interval. In a prostate case the time between the acquisition of the first medical image and the second medical image will be in the order of 5-15 minutes. The second medical image could be a T2w MRI image. This T2w image could be used by a clinician to delineate the treatment target volume 209. Treatment objectives will be set for the treatment target. The delineated treatment target and its treatment objective will serve as an input for the calculation of the radiotherapy plan 207.

Determining of positions of the first location 312 (FIG. 3) and the second location 314 (FIG. 3) in the first medical image and in the second medical image 203. The first location and second location could be positioned on a contour line 304 (FIG. 3) around a structure of interest, but could also be individual landmarks. Preferably, segmentations of one or more structures of interest are used to identify the first location, second location and further locations, as can be seen in FIG. 3 wherein a bladder 304, prostate 302 and rectum 308 are segmented based on the first medical image. Contours 306 and 310 in FIG. 3 represent the segmentations of the bladder and bowel respectively, based on their positions and shapes in the second medical image.

Using the determined positions for determining the patient specific locally varying margin 316, 318 around the treatment target and/or organ at risk 204. This could for example be the distance between the first contour and second contour or an interpolated or extrapolated version thereof. Also the patient specific locally varying margin could be a distance between a first hull comprising the first location and second location and a second hull comprising the first and second location. In the given example, the margin is defined on anchor points of a triangulated surface mesh and is de-facto contuously varying around the structure.

calculating a radiotherapy plan using the patient specific locally varying margin 207.

Figure 4:
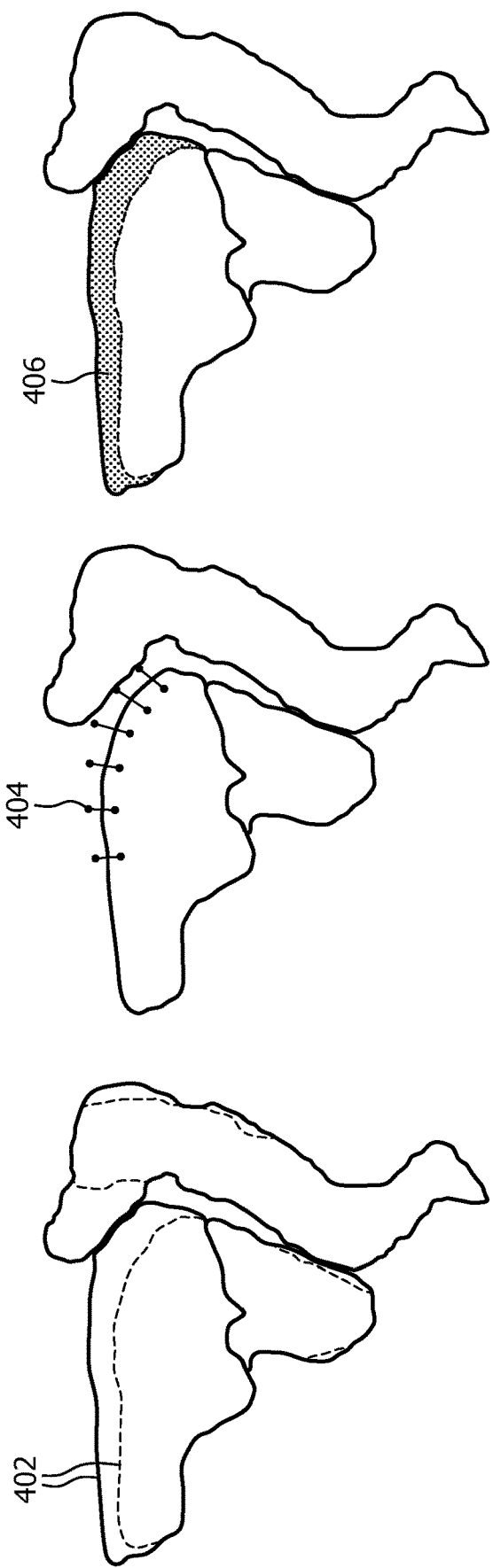

The displacement of the first location, second location and optionally further locations can be displayed to a user in many different ways. FIG. 4 shows a few examples of how the displacement of the first location, second location and optionally further locations can be displayed to a user. For example the displacement can be displayed by an overlay of two segmentations 402. Alternatively, displacement vectors could be displayed to the user 404. Also, line thickness can be varied to indicate the extent of displacement 406.

Figure 5:
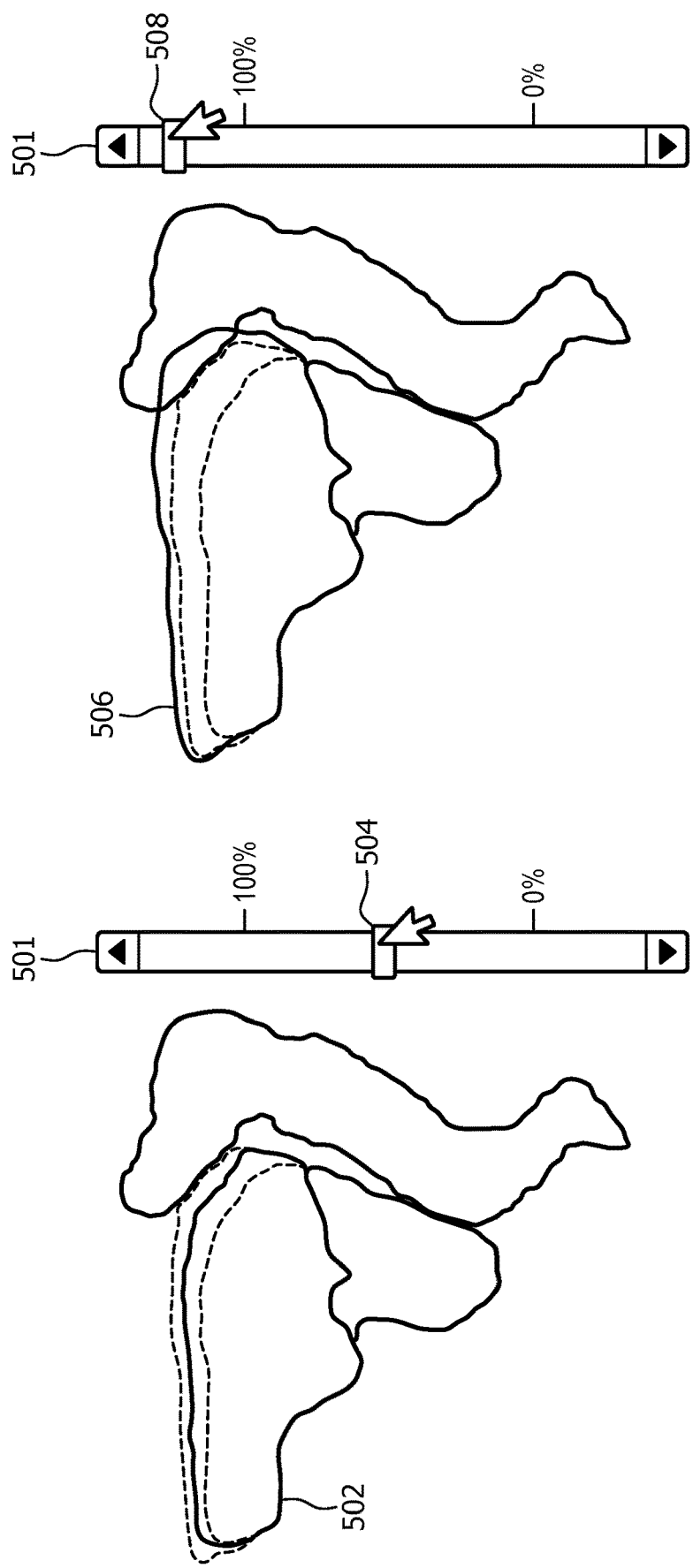
FIG. 5 illustrates diagrammatically an example of how an interpolation and extrapolation of the contour can be displayed to the user.

FIG. 5 illustrates diagrammatically an example of how an interpolation and extrapolation of the contour 502, 506 can be displayed to the user. In this example a slider 501 is provided by which means the user can indicated what interpolated or extrapolated contour he wishes to see. A slider position at 50% 504 shows contour 502. A slider position at 120% 508 shows contour 506. The user can use this information to decide which of these margins he wants to use during treatment in order to compensate for intrafraction motion. Also he may decide to use multiple margins during a single fraction. For example he could start with a margin to compensate for the intrafraction motion which is slightly larger than the 0% contour, later in the fraction the margin to compensate for the intrafraction motion could be set at slightly larger than 50% and toward the end of the fraction the margin could be set at slightly larger than 100%. These values are purely exemplary, other values could be chosen as well. These multiple margins could be incorporated in the radiotherapy plan.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A method for determining a patient specific locally varying margin on a treatment target and/or an organ at risk in order to compensate for local intrafraction motion expected during a radiotherapy fraction to be delivered over a radiotherapy fraction time interval, wherein the patient specific locally varying margin is determined based on a displacement and/or an estimate for the displacement of at least a first location and a second location on the treatment target and/or organ at risk, the method comprising:

acquiring a first medical image of the treatment target and/or the organ at risk, wherein the first medical image is a magnetic resonance image (MRI) suitable to be used for a generation of a pseudo CT image of the treatment target;

acquiring a second medical image of the treatment target and/or the organ at risk, wherein the time between the acquiring of the first medical image and the second medical image is approximately the same as the radiotherapy fraction time interval;

determining of positions of the first location and the second location in the first medical image and in the second medical image; and using the determined positions for determining the patient specific locally varying margin around the treatment target and/or organ at risk, wherein the patient specific locally varying margin is determined based on multiple locations defining a first contour around the treatment target or organ at risk in the first medical image and defining a second contour around the treatment target or organ at risk in the second medical image.

2. A method for determining a patient specific locally varying margin as claimed in claim 1, further comprising the step of calculating a radiotherapy plan using the patient specific margin.

3. A method for determining a patient specific locally varying margin as claimed in claim 2, wherein multiple margins are determined, such that during the radiotherapy fraction time interval, a time dependent margin can be used and wherein the multiple margins are taken into account for the calculation of the radiotherapy plan.

4. A method for determining a patient specific locally varying margin as claimed in claim 1, wherein the second medical image is an image suitable to be used for segmentation of the treatment target.

5. A method for determining a patient specific locally varying margin as claimed in claim 4, wherein the second medical image is a T2w image.

6. A method for determining a patient specific locally varying margin as claimed in claim 4, further comprising a step calculating an interpolated position and/or extrapolated position of the first location and the second location and displaying the interpolated position and/or extrapolated position to a user.

7. A method for determining a patient specific locally varying margin as claimed in claim 1, wherein the first image is one out of a T1-DIXON image, a UTE-DIXON image.

8. A method for determining a patient specific locally varying margin as claimed in claim 1 further comprising a step of displaying a displacement of the first location and a displacement of the second location between the acquiring of the first medical image and the acquiring of the second medical image to a user.

9. A method for determining a patient specific locally varying margin as claimed in claim 1, wherein the position of the first location and second location are determined based on segmentation of the treatment target.

10. A tangible, non-transitory computer readable medium for determining a patient specific locally varying margin around a treatment target and/or organ at risk, wherein the tangible, non-transitory computer readable medium stores instructions, which when executed by a computer, cause the computer to:

determine of a position of a first location and second location on a treatment target and/or organ at risk in a first medical image and in a second medical image, wherein the first medical image is an MRI image suitable to be used for a generation of a pseudo CT image of the treatment target; and use the determined positions for determining the patient specific locally varying margin around the treatment target and/or organ at risk, wherein the patient specific locally varying margin is determined based on multiple locations defining a first contour around the treatment target or organ at risk in the first medical image and defining a second contour around the treatment target or organ at risk in the second medical image.

11. The tangible, non-transitory computer readable medium as claimed in claim 10 wherein the instructions when executed by the computer, further cause the computer to:

acquire the first medical image of the treatment target and/or organ at risk; and acquire the second medical image of the treatment target and/or organ at risk, wherein a time between the acquisition of the first medical image and the second medical image is approximately the same as to a radiotherapy fraction time interval.

12. A medical imaging system, comprising:

a processor;

a tangible, non-transitory memory that stores instructions, which when executed by the processor, cause the processor to:

determine of a position of a first location and a second location on a treatment target and/or organ at risk in a first medical image and in a second medical image, wherein the first medical image is an MRI image suitable to be used for a generation of a pseudo CT image of the treatment target; and use the determined positions for determining a patient-specific locally varying margin around the treatment target and/or organ at risk, wherein the patient specific locally varying margin is determined based on multiple locations defining a first contour around the treatment target or organ at risk in the first medical image and defining a second contour around the treatment target or organ at risk in the second medical image.

13. The medical imaging system as claimed in claim 12, wherein the instructions when executed by the processor, further cause the processor to:

acquire the first medical image of the treatment target and/or organ at risk; and acquire the second medical image of the treatment target and/or organ at risk, wherein a time between the acquisition of the first medical image and the second medical image is approximately the same as a radiotherapy fraction time interval.

14. The medical imaging system as claimed in claim 12, wherein the instructions, when executed by the processor, further cause the processor to determine the patient-specific locally varying margin based on multiple locations defining a first contour around the treatment target or organ at risk in the first medical image, and defining a second contour around the treatment target or organ at risk in the second medical image.

15. The medical imaging system as claimed in claim 12, wherein the instructions, when executed by the processor, further cause the processor to calculate a radiotherapy plan using the patient-specific margin.

16. The medical imaging system as claimed in claim 15, wherein the instructions, when executed by the processor, further cause the processor to determine multiple margins, such that during the radiotherapy fraction time interval, a time dependent margin is used, and the multiple margins are taken into account for the calculation of the radiotherapy plan.

17. A controller, comprising:
a processor;
a tangible, non-transitory memory that stores instructions, which when executed by the processor cause the processor to:
determine of a position of a first location and second location on a treatment target and/or organ at risk in a first medical image and in a second medical image, wherein the first medical image is an MRI image suitable to be used for a generation of a pseudo CT image of the treatment target; and
use the determined positions for determining a patient-specific locally varying margin around the treatment target and/or organ at risk, wherein the patient specific locally varying margin is determined based on multiple locations defining a first contour around the treatment target or organ at risk in the first medical image and defining a second contour around the treatment target or organ at risk in the second medical image.

18. The controller as claimed in claim 17, wherein the instructions, when executed by the processor, further cause the processor to:
acquire the first medical image of the treatment target and/or organ at risk; and
acquire the second medical image of the treatment target and/or organ at risk, wherein a time between the acquisition of the first medical image and the second medical image is approximately the same as to a radiotherapy fraction time interval.

19. The controller as claimed in claim 18, wherein the instructions, when executed by the processor, further cause the processor to determine a patient-specific locally varying margin based on multiple locations defining a first contour around the treatment target or organ at risk in the first medical image, and defining a second contour around the treatment target or organ at risk in the second medical image.

20. The controller as claimed in claim 18, wherein the instructions, when executed by the processor, further cause the processor to calculate a radiotherapy plan using the patient-specific margin.

21. The controller as claimed in claim 20, wherein the instructions, when executed by the processor, further cause the processor to determine multiple margins, such that during the radiotherapy fraction, a time dependent margin is used, and the multiple margins are taken into account for the calculation of the radiotherapy plan.

* * * * *